United States Patent [19]  [11]  4,197,647
Goldenthal  [45]  Apr. 15, 1980

[54] DENTAL PLIERS
[76] Inventor: Edgar J. Goldenthal, 240 Central Park South, New York, N.Y. 10019
[21] Appl. No.: 893,095
[22] Filed: Apr. 3, 1978

Related U.S. Application Data
[63] Continuation-in-part of Ser. No. 740,986, Nov. 11, 1976, abandoned.
[51] Int. Cl.² ............................................. A61C 3/16
[52] U.S. Cl. ........................................ 433/159; 81/421
[58] Field of Search ............... 32/61, 62, 43, 44, 45; 128/321, 322, 324; 81/421

[56] References Cited
U.S. PATENT DOCUMENTS

| | | | |
|---|---|---|---|
| 511,067 | 12/1893 | Walter | 32/62 |
| 772,324 | 10/1904 | Asdell | 32/62 |
| 784,098 | 3/1905 | Beazley | 32/44 |
| 1,626,226 | 4/1927 | Cantor | 32/62 |
| 1,913,770 | 6/1933 | Olenik | 128/321 |
| 2,937,446 | 5/1960 | Weisenfeld | 32/43 |
| 3,503,397 | 3/1970 | Fogarty et al. | 81/421 |
| 3,866,610 | 2/1975 | Kletschka | 128/322 |
| 3,898,738 | 8/1975 | Linder | 32/62 |

OTHER PUBLICATIONS
"New Instrument for Removing Crowns and Impressions," Dental Abstrats., vol. 8 #9, 9-1963, p. 551.

*Primary Examiner*—Louis G. Mancene
*Assistant Examiner*—John J. Wilson
*Attorney, Agent, or Firm*—Blum, Kaplan, Friedman, Silberman & Beran

[57] ABSTRACT

Curved dental pliers particularly suited for removing crowns and other dental prostheses are scissors-like or nut-cracker-like in action, the scissors-like pliers having a pair of fulcral projections to the rear of the pivot joint and the others having a fulcrum at the pivot. The fulcral projections locate a proper fulcral point and provide for proper orientation in the arc of removal. The pliers include interchangeable removable cushioning pads for gripping the dental work without damaging same. A support member for use in conjunction with the pliers provides a firm base for receiving the thrust of the fulcral projections.

18 Claims, 13 Drawing Figures

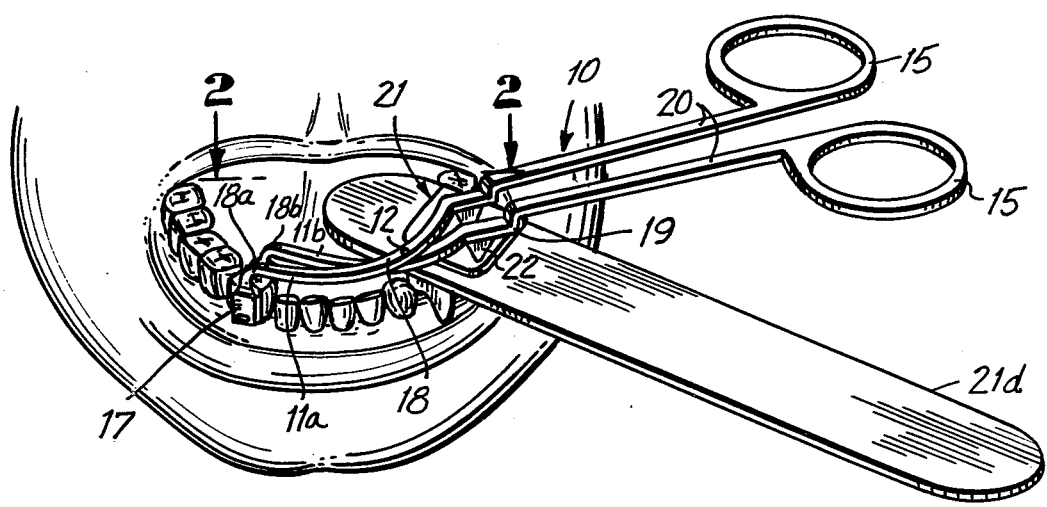
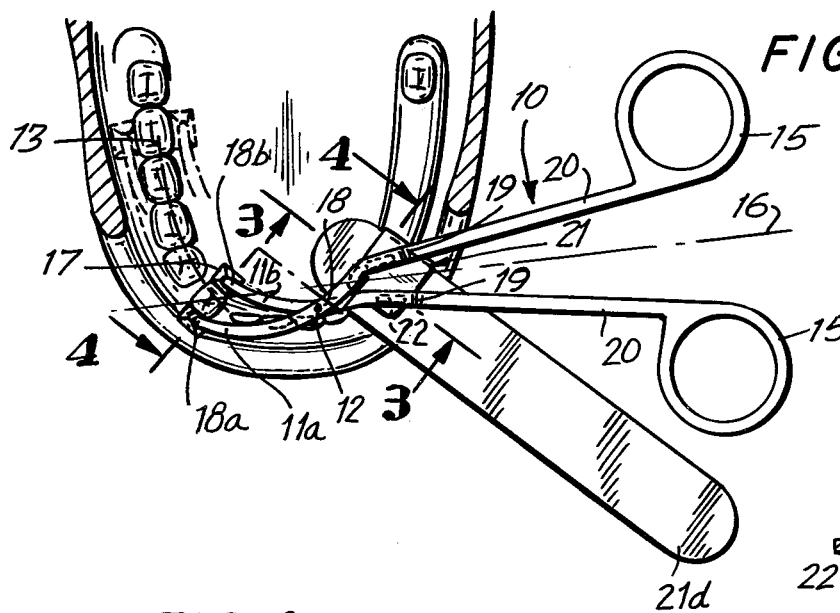
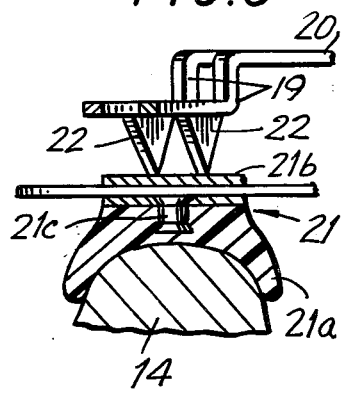
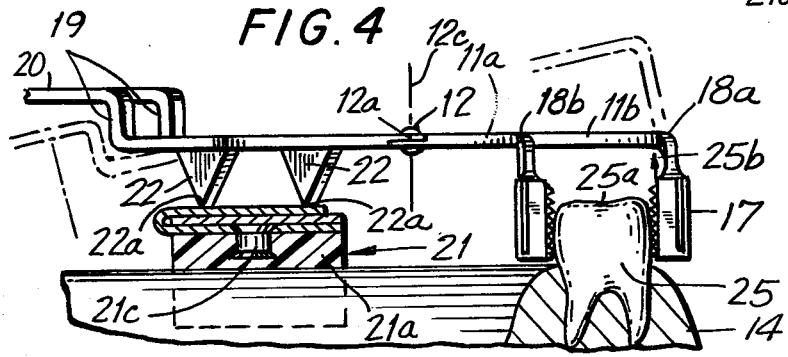

DENTAL PLIERS

CROSS REFERENCE TO RELATED APPLICATION

The present application is a continuation-in-part application of my co-pending application Ser. No. 740,986 filed Nov. 11, 1976 for DENTAL PLIERS, and now abandoned.

BACKGROUND OF THE INVENTION

This invention relates generally to improved pliers for facilitating the handling of dental prostheses and in particular to pliers for facilitating the insertion and removal of dental crowns. Heretofore, pliers-like devices designed for handling dental prostheses such as crowns and the like have generally been less than completely satisfactory for several reasons. One problem particularly troublesome to dentists is the failure of such pliers to provide sufficient sensitivity for permitting soft hand impressions formed from compounds, rubber, wax or silicone to be removed and inserted without causing damage to the impression. Similarly the lack of sensitivity in such pliers does not permit same to be used in handling easily-breakable dental crowns and/or dental bridgework. Also, such pliers for removing dental prostheses are not adjustable to different tooth sizes. Finally, such dental pliers are unable to impart a sufficient force in the direction of the long axis of the tooth for removing the crown or bridge work without the possiblity of causing damage to the prostheses or to the teeth surrounding same. Accordingly, a dental pliers capable of removing and inserting dental crowns and the like and that eliminates the above-noted problems is needed.

SUMMARY OF THE INVENTION

Generally speaking, in accordance with the invention, curved pliers for removing dental crowns and the like having removable resilient cushions and fulcral projections are provided. The pliers include two arms pivotably joined in generally scissors-like fashion or in nut-cracker-like fashion. The clamping jaw of each arm includes a receptacle into which the resilient cushions are respectively inserted. Each arm, in the scissors-like embodiment includes an extending projection disposed proximate to the pivotal joint to serve as a fulcrum in the removal of dental prostheses by the clamping ends of the arms. Intermediate the handle end of the arms and the fulcral projections, the arms are stepped to define an offset for improving handling of the dental prostheses by the pliers. Also, the arms are curved in a plane essentially perpendicular to the direction in which said crown or bridge-work is to be removed, this curvature providing for placement of the fulcral projections directly over or below the center of the dental ridge on the maxillary or mandibular jaws. As will be evident, two sets of such pliers are needed, said pliers being curved in opposing directions. The nut-cracker-like pliers have a fulcral projection at the pivot and clamping jaws between the pivot and the handle ends. While the nut-cracker-like pliers may be provided in two sets with opposite curvatures, generally, it has been found that a single set suffices, said nut-cracker-like pliers preferably being used for the anterior portions of the jaws and the scissors-like pliers being used for the posterior portions of the jaws.

Accordingly, it is an object of this invention to provide improved dental pliers for removing dental prostheses without damaging same.

Another object of the instant invention is to provide dental pliers capable of utilizing a fulcrum effect to flatten the arc of removal of the prostheses.

A further object of the invention is to provide dental pliers with scissoring arms which are curved so that fulcral projections on said arms may be positioned in registry with the dental ridge of the maxillary or mandibular jaws respectively.

Still another object of this invention is to provide dental pliers that have a removable cushioned insert for use with teeth in various sizes and shapes.

Yet another object of this invention is to provide curved pliers of nut-cracker-like construction for removal of prostheses from anterior teeth.

Still other objects and advantages of the invention will in part be obvious and will in part be apparent from the specification.

The invention accordingly comprises the features of construction, combinations of elements, and arrangement of parts which will be exemplified in the constructions hereinafter set forth, and the scope of the invention will be indicated in the claims.

For a fuller understanding of the invention, reference is had to the following description taken in connection with the accompanying drawings, in which:

FIG. 1 is a perspective view of curved dental pliers in accordance with an embodiment of the instant invention in combination with a fulcral block adapted for holding a flat blade and supporting the fulcral projections of the pliers;

FIG. 2 is a plan view of the pliers of the embodiment of FIG. 1;

FIG. 3 is a view taken along line 2—2 of FIG. 2;

FIG. 4 is a view taken along line 4—4 of FIG. 2;

DESCRIPTION OF THE PREFERRED EMBODIMENTS

Figure 5:
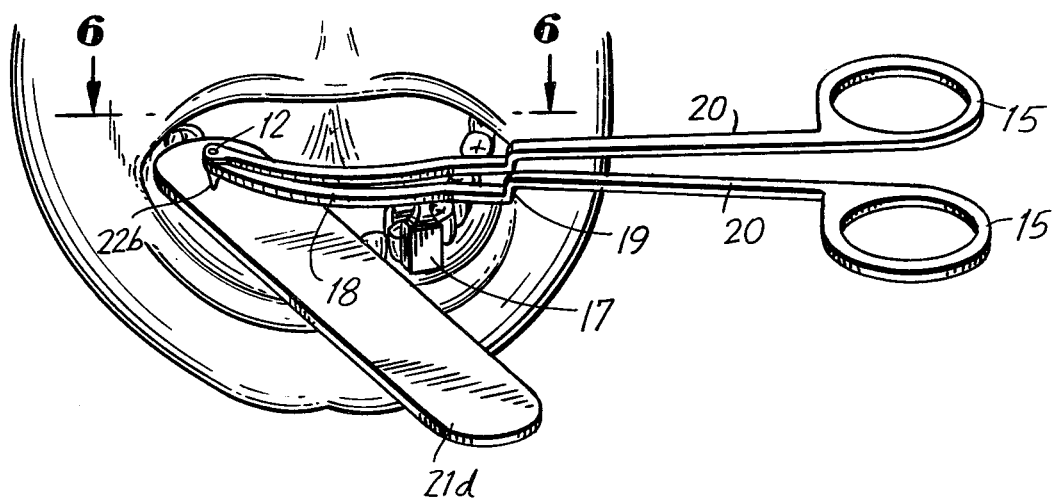
FIG. 5 is a perspective view of another embodiment of the invention.

Referring now to FIG. 1, curved pliers in a scissors-like construction, generally indicated by the reference numeral 10, for removing dental crowns and the like are depicted. The pliers 10 comprise two curved arms 11a and 11b pivotably joined at pivot 12 to define a scissors-like implement, the arms rotating about axis 12c in pivot 12 (FIG. 4). It should be noted that said curved arms 11a and 11b lie essentially in a single plane, defining said plane. Each of the arms 11a and 11b has a handle portion 20 terminating in finger rings 15. The arms also have clamping ends 18a and 18b respectively, each clamping end having a clamping receptacle 17 disposed thereat. Each clamping receptacle is adapted for holding a cushioned insert which preferably is serrated.

The portion of the pliers from the clamping ends 18a and 18b to the fulcral projections 22 is designated as the clamping portion of the pliers and the portion of the pliers from each fulcral projection to the finger rings is designated as the handle portion. Preferably, the fulcral projections are close to the pivot 12 in order to provide as much leverage as possible in removing a dental prosthesis. The clamping portion 18 for clamping ends 18a and 18b to fulcral projections 22 is curved as aforenoted; handle portions 20 are disposed relative to clamping portion 18 so as to lie away from the cheek of a patient when the pliers are in use, and, except for a step portion 19, preferably being straight. The preferred direction of the handles is such that, when the handles are together, the common line defined by same passes immediately above fulcral projections 22 and handle ends 18a and 18b. This line is given the reference numeral 16 in FIG. 2, and, as can be seen, said line 16 bisects the angle between handles 20 and passes between fulcral projections 22 and clamping ends 18a and 18b. The advantage of this construction is that when a downward or upward pressure is applied to either of the embodiments disclosed herein, there is no tendency for the pliers to rotate around this line; consequently, a single fulcral projection 22 can serve for precise and effective use of the pliers.

The curvature of the clamping portion 18 of the pliers should approximate that of the array of teeth in a jaw, the dental ridge in a jaw being indicated by dashed line 13 of FIG. 2. This curvature varies over the length of the dental ridge and also varies between patients. The radius of this curvature is about 1 inch, and this is a preferred radius of curvature for clamping end 18 of the pliers of the present invention. Also, it is desirable that a step 19 be provided for maintaining clearance between the handle portions 20 of the pliers and the teeth during operation of the pliers. Preferably, step portion 19 is at right-angles to handle portion 20.

FIGS. 1 through 4 show a fulcral block for use in combination with pliers 10 where a tooth is missing at the location where fulcral projections 22 are to be positioned. In such a case, the fulcral block consisting of a fulcral mount and a fulcral frame are positioned over a gum 14 with the mount 21a making direct contact with the gum 14. A frame 21b is mounted by means of a swivel 21c on the mount 21a. The frame 21b is adapted for holding a flat blade 21d therein. The blade is held by the operator of the pliers and serves to stabilize the fulcral block. In addition, if the operator should inadvertently rotate the pliers around the clamping ends, thereby carrying the fulcral projections 22 away from the fulcral block 21, then the blade will serve to support the pliers by means of the fulcral projections 22. It should be noted that the fulcral block 21 is used only when a tooth is missing at the region where the fulcral projections are to be brought to bear. The fulcral block serves to insure that rotation of the pliers during the step of removal of a prosthesis will occur around an axis which is at the level of the biting surface of the remaining teeth. Where a tooth is present at the region in which the fulcral projections are to be brought to bear, then the fulcral block is not used, and, instead, a flat blade such as a tongue depressor, is placed directly on the tooth. The way in which the fulcral block 21 is used for bearing upon a gum 14 is shown in FIGS. 3 and 4, respectively taken along broken lines 3—3 of FIG. 2 and 4—4 of FIG. 2. Attention is called to the fact that location of ends 22a of fulcral projections 22 at the level of the biting surface 25a of a prosthesis 25 results in extraction of the prosthesis in the direction indicated by the arrow 25b along the length of the prosthesis. Consequently, possible damage to the gum is avoided.

Figure 6:
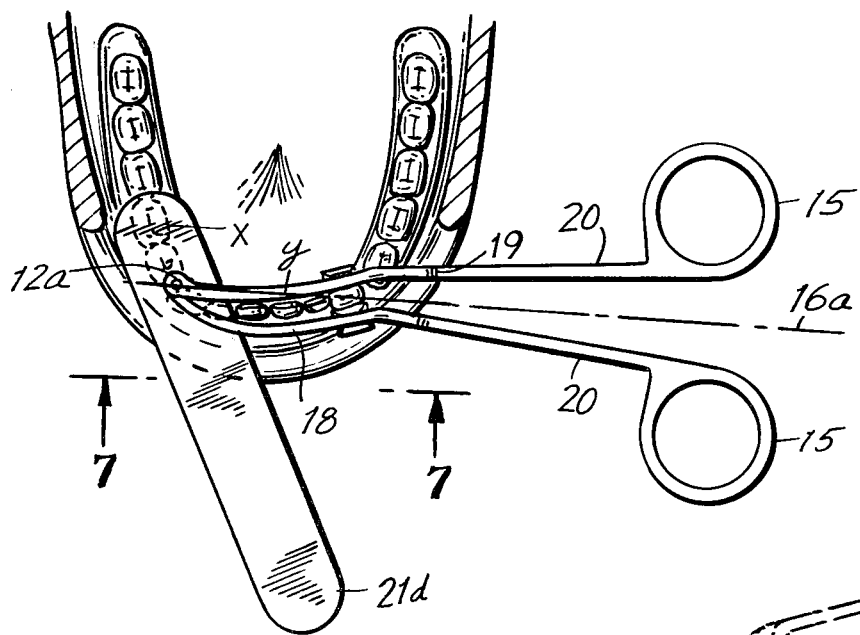
FIG. 6 is a plan view of the embodiment of FIG. 5 taken in the direction of the arrow 6—6.
Figure 7:
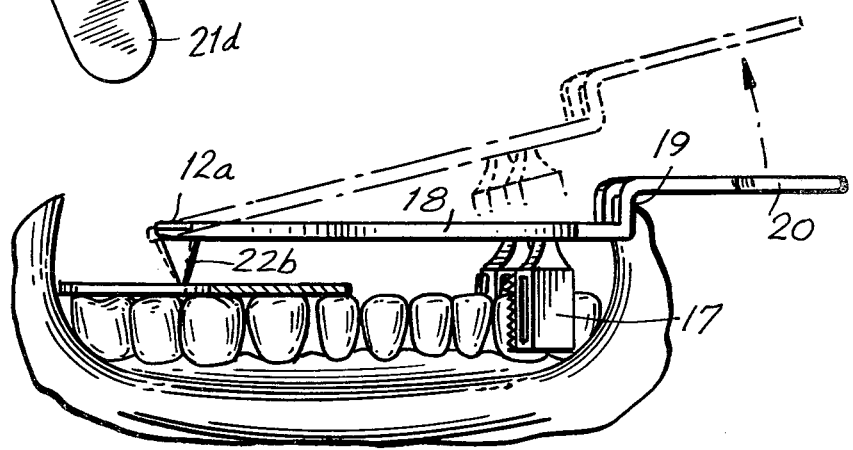
FIG. 7 is a view taken along line 7—7 of FIG. 6.
Figure 8:
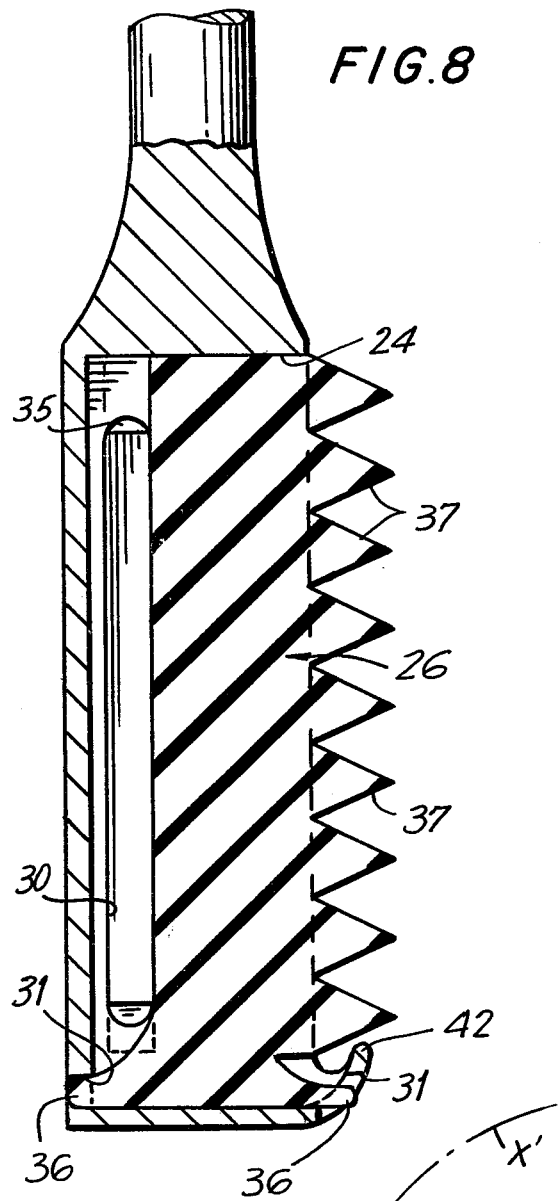
FIG. 8 is a view of a clamping receptacle and cushioned insert therefor of the dental pliers depicted in FIGS. 1 and 5.
Figure 9:
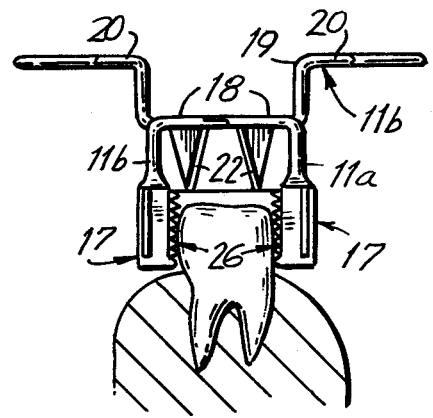
FIG. 9 is a view in partial section along the array of teeth in a mandibular jaw.

A second embodiment of the invention is shown in FIGS. 5-7 in which the pliers are in a nut-cracker-like configuration. In this second embodiment the fulcral projections may also be disposed proximate the pivot. However, it is preferred that the pivot include a fulcral projection as part thereof, this construction being shown in FIGS. 5 and 7, the pivot itself being indicated by the reference numeral 12a and the fulcral projection by the reference numeral 22b.

This second embodiment is particularly useful for removal of prostheses in the anterior portion of the mouth. While the pliers of the first embodiment can be used for removal of a prosthesis from the anterior portion of the mouth, this first embodiment is not so convenient as the pliers of the second embodiment. The pliers of the first embodiment would lie inconveniently close to the cheek when used on a prosthesis near the anterior portion of the jaw.

The curvature of the pliers in the embodiment of FIGS. 1 and 2 is such that they are more conveniently used for the right mandibular jaw and the left maxillary jaw. Accordingly, where curved dental pliers in accordance with the present invention are to be used in connection with prostheses in the left mandibular jaw and the right maxillary jaw, the pliers should be curved in the opposite direction to those shown in FIGS. 1 and 2. Similarly, with respect to the pliers of the second embodiment shown in FIGS. 5 and 6, pliers with the opposite curvature may also be employed. However, I have found that while two pairs of pliers of opposite curvature are preferably made available for use in connection with the posterior part of the jaws, a single pair of pliers of either curvature will serve for the anterior teeth. The pliers of the second embodiment as shown in FIGS. 5 and 6 can clamp on a prosthesis wherever it is located in the anterior portion of the jaw and will remove the prosthesis in the lengthwise direction thereof as shown in FIG. 7, pivoting around the end of fulcral projection 22b.

Figure 10:
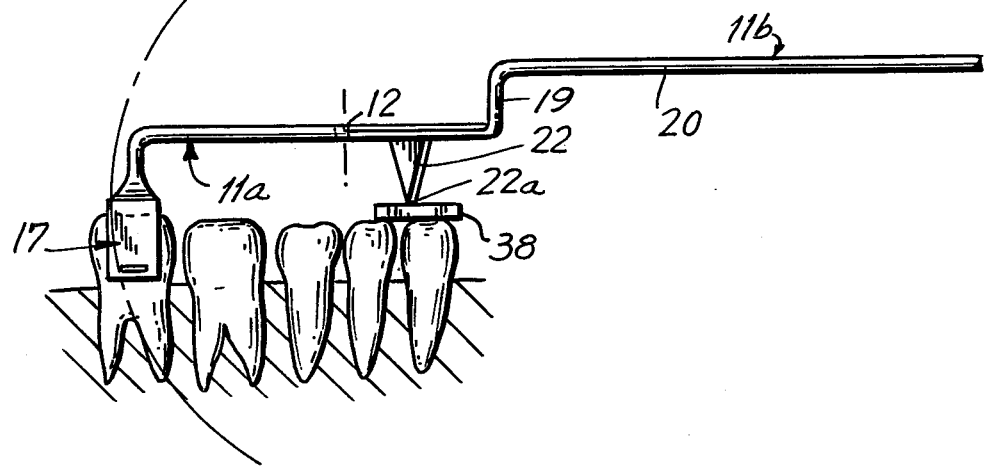
FIG. 10 illustrates the direction in which a prosthesis is moved relative to the length of a tooth, said prosthesis being removed by pliers within the scope of the present invention.
Figure 11:
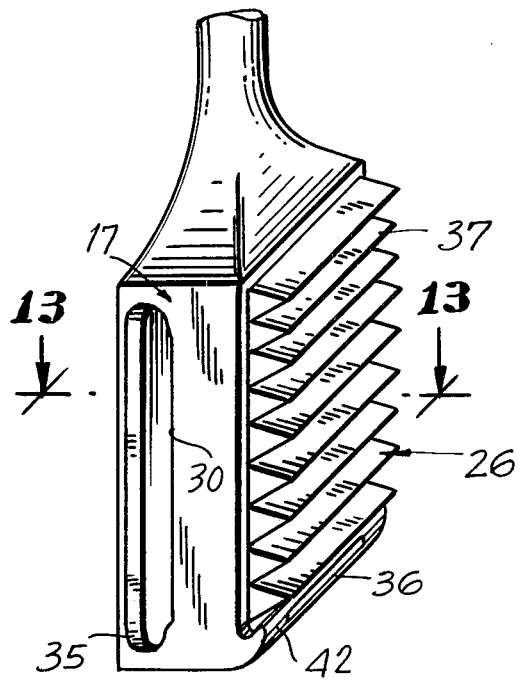
FIG. 11 is a perspective view of a clamping receptacle containing a cushioned insert.
Figure 12:
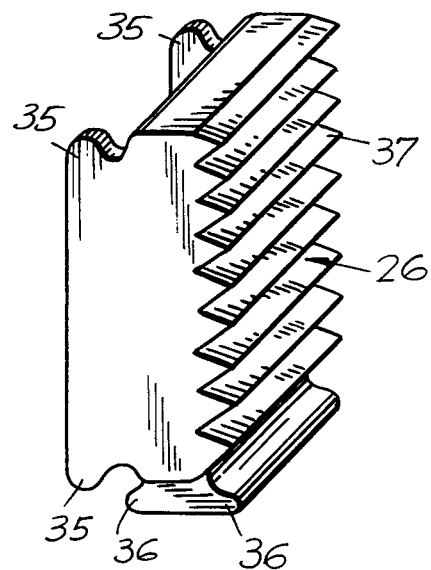
FIG. 12 is a perspective view of a cushioned insert for said clamping receptacle.
Figure 13:
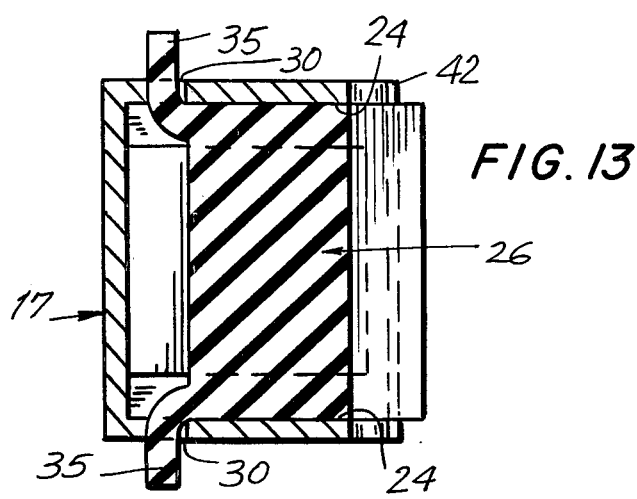
FIG. 13 is a view taken along line 13—13 of FIG. 11.

In use of pliers of either embodiment, the pliers are closed over a crown or the like dental prosthesis so that one of the cushioned inserts 26 is pressed against the buccal (facial) surface of the dental crown and the other cushioned inert 26 is pressed against the lingual (palatal) surface of the dental crown. A tongue depressor blade 38 (FIG. 10) or similar broad flat object may be placed beneath the fulcral projections 22 to assist in removal of the prosthesis. As aforenoted, the fulcral projections 22 are positioned to orient the arc of removal so that the tangent to the arc is substantially co-linear at the removal position with the lengthwise extent of the tooth. As illustrated in FIG. 10, arc x' is formed by use of end 22a of the fulcral projections as the fulcral point. The tangent to the arc is indicated by arrow 5. If the pliers of the instant invention were formed without the fulcral projections 22, the position about which the pliers rotates during removal of a prosthesis would be indefinite and the pliers could shift during the course of a removal, thereby decreasing the ease and delicacy with which a prosthesis can be removed, thereby increasing the likelihood of damage to the dental crown or the like and to the teeth surrounding same during removal of said prosthesis.

Referring now to FIGS. 8 and 11-13, clamping receptacle 17 is formed with an opening 24 for receiving cushion insert 26 having ridges 35 and 36 thereon. Clamping receptacle 17 is substantially rectangular and forms a five-walled chamber. The side and bottom walls of the clamping receptacle have openings 30 and 31 therein for receiving ridges 35 and 36 for the cushioned insert 26 and designed to releasably secure the cushioned inserts 26 in the receptacle. Ridges 35 and 36 eliminate any wobble when the cushioned inserts are inserted in the clamping receptacle and also aid in releasably securing the cushioned inserts in the clamping receptacles. The clamping receptacles 17 further include a lip 42 for adding a firmer support to the lower portion of the cushioned inserts 26 at the gingival region of a tooth. The portion of the cushioned inserts 26 that contacts the prosthesis has a series of flexible serrations 37 forming a protective surface to be placed against the crown or other prosthesis thus providing a firm gripping by the clamping receptacles when the dental prosthesis is to be removed.

The cushioned inserts 26 can be made of varying widths to fit narrow anterior teeth or wider posterior teeth. It is noted however that the rearward portion of the cushioned inserts 26 that fit into the clamping receptacle remain constant in size. This feature further adds to the versatility of the pliers constructed in accordance with the instant invention since two pairs of pliers of opposite curvatures, with a variety of inserts, will serve for removing prostheses made for teeth of different sizes and shapes where the teeth are in the posterior part of the mouth, and a single pair of pliers will serve for removal of prostheses made for teeth of different sizes and shapes where the teeth are in the anterior portion of the mouth. The cushioned inserts 26 are easily inserted or removed from the clamping receptacles by finger pressure and hence readily permit sterilization and replacement. Although rubber is a preferred material for forming the cushioned inserts, they can be formed of any resilient material that is flexible, pliable and soft and non-absorbant.

The preferred material for the construction of the pliers is surgical stainless steel. This allows the pliers to be sterilized with the use of an autoclave. The cushioned inserts are generally cold sterilized. However certain plastics are also autoclavable for a reasonable number of times before they lose their pliability.

A preferred embodiment of the instant invention formed from surgical stainless steel provides arms having a total length of about 14 cm. The distance from the fulcral projection to the clamping receptacles measured along the arc of the clamping portion was 4.5 cm. In the scissors-like embodiment, the distance from the fulcral projections to the pivot was about 1.5 cm. The length of the fulcral projection is preferably about 10 mm. However, it is noted that the dimensions contained herein are by way of example only, and that such dimensions may vary in accordance with the teachings of the instant invention.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. Dental pliers for removal of a dental, prosthesis from a tooth in the mouth, comprising:
    a pair of arms, each arm having a clamping portion and a handle portion, each clamping portion having a clamping section;
    clamps means comprising a clamping receptacle for holding therein a cushioning insert on said clamping section of each arm, said clamp means being position for cooperating with each other in seizing and releasing a prosthesis;
    pivot means joining said arms for rotation relative to each other, said clamping portions, exclusive of said clamp means, lying in a single plane perpendicular to said pivot means and each having a curvature approximating that of the dental arch in a mouth, the curvatures of said clamping portion being in the same direction in said plane, said clamp means extending from said clamping section in a direction perpendicular to said plane and thus parallel to said pivot means; and
    fulcral projection means extending from one of said pivot means and an arm, said fulcral projection means being positioned for rotation of said pliers for removal of a prosthesis from a tooth, the direction of removal of said prosthesis being initially parallel to the long axis of said tooth, and said handle portions being disposed relative to said clamping portion for avoiding interference with the cheek of a patient.

2. Dental pliers as defined in claim 1, wherein the radius of curvature of said arms is about 1 inch.

3. Dental pliers as claimed in claim 1, wherein said dental pliers are scissors-like in construction and said clamp means are disposed at the end of each arm other than at said handle portion, said fulcral projection means being disposed intermediate said pivot means and said handle portion of said arm.

4. Dental pliers as claimed in claim 3, wherein said clamping portion extends approximately from said fulcral projection means to said clamp means, said handle portion being the remainder of each of said arms, said handle portion including a stepwise bent portion to render the lengthwise extent of said clamping portions and handle portions offset with respect to each other.

5. Dental pliers as claimed in claim 4, wherein said stepwise bent portion is perpendicular with respect to the lengthwise extent of said clamping portion and handle portion of each arm, each of said handle portions of said arms being essentially straight from said stepwise bent portion in a direction away from said pivot means.

6. Dental pliers as claimed in claim 1, wherein said fulcral projection means is disposed proximate said pivot means.

7. Dental pliers as claimed in claim 1, wherein said dental pliers is nut-cracker-like in construction, said pivot means joining said arms at one end of each arm, said fulcral projection means being proximate said pivot means and said clamp means being disposed between said fulcral projection means and the other end of each of said arms.

8. Dental pliers as claimed in claim 7, wherein said handle portion includes a stepwise-bent portion to render the lengthwise extent of said clamping portions and handle portions offset with respect to each other.

9. Dental pliers as claimed in claim 1, wherein said clamp means includes, cushioning inserts adapted to be releasably secured to said clamping receptacle, said cushioning inserts providing a firm but gentle hold on a prosthesis.

10. Dental pliers as claimed in claim 9, wherein said receptacle has a first opening for releasably receiving said cushioning inserts in said receptable and further openings in same, said cushioning insert including ridges adapted to be inserted in said further openings to further releasably secure said, cushioning inserts in said receptable.

11. Dental pliers as claimed in claim 1, further comprising a fulcral block for providing support for said fulcral projection means during use of said pliers, said fulcral block comprising a support frame for receiving and holding a flat blade, a support mount for spacing said support frame from a dental ridge of a patient and swivel means joining said frame to said mount, said fulcral block being intended for use where said fulcral projection means are to be positioned in a location lacking a tooth, said fulcral block having an overall height such as to position the outer end of said fulcral projection means at the level of the biting surface of the remaining teeth.

12. Dental pliers as claimed in claim 1 wherein said dental pliers is in one of a first and second configuration with respect to the direction of curvature of said arms, said pliers in said first configuration being preferable for removing prostheses in the left mandibular and right maxillary jaws, said pliers in said second configuration being preferable for removing prostheses in the right mandibular and left maxillary jaws.

13. Dental pliers comprising
a pair of curved arms, each having a clamping portion and a handle portion adjoining each other said clamping portion having two ends;
pivot means at one end of said clamping portion, said pivot means having an axis and joining said arms for rotation relative to each other about said axis, said clamping portions of both of said arms being curved in a plane perpendicular to said axis and in the same direction, the curvature of each of said arms approximating that of the dental arch in a mouth;
opposable clamp means at the other end of each of said clamping portions, said clamp means extending perpendicularly to said plane and each including a clamping receptacle for holding therein cushioning insert means; and
fulcral projection means extending from said arms proximate the junctions between said clamping portion and handle portion, and extending in a direction parallel to said axis,
said handle portions each having a straight portion so directed that
a plane bisecting the angle between straight portions and parallel to said axis also bisects said fulcral projection means and the space between said opposable clamp means, whereby any tendency to tip to one side of said plane or the other or interference with the cheek in the use of same when removing said prosthesis is avoided.

14. Dental pliers as claimed in claim 13, wherein said clamping receptacle has a first opening for releasably receiving said cushioning insert means and further comprising said cushioning insert means.

15. Dental pliers as claimed in claim 14, wherein said clamping receptacle includes further openings, and wherein said cushioning insert means include ridges for engaging the walls of said further openings.

16. Dental pliers as claimed in claim 15, wherein said clamping receptacle has two ends, one end joining said receptacle to said clamping portion and the other end has a lip for firmly supporting a portion of said cushioning insert means proximate thereto and for engaging a prosthesis proximate the gingival surface of said tooth.

17. Dental pliers as claimed in claim 14, wherein each said cushioning insert includes serrations on the face thereof, said serrations extending from said first opening in said receptacle when said insert is in said receptacle.

18. Dental pliers as claimed in claim 14, wherein said cushioned inserts are non-absorbent and non-porous.

* * * * *